(12) United States Patent
Lindorfer

(10) Patent No.: US 8,295,431 B2
(45) Date of Patent: Oct. 23, 2012

(54) NON-CONTACTING ROTARY JOINT

(75) Inventor: Stephan Lindorfer, Müchen (DE)

(73) Assignee: Non-Contacting Rotary Joint, Fürstenfeldbruck (DE)

( * ) Notice: Subject to any disclaimer, the term of this patent is extended or adjusted under 35 U.S.C. 154(b) by 223 days.

(21) Appl. No.: 12/664,548

(22) PCT Filed: May 28, 2008

(86) PCT No.: PCT/EP2008/056558
§ 371 (c)(1),
(2), (4) Date: Jun. 15, 2010

(87) PCT Pub. No.: WO2008/155200
PCT Pub. Date: Dec. 24, 2008

(65) Prior Publication Data
US 2010/0310039 A1    Dec. 9, 2010

(51) Int. Cl.
*H05G 1/08* (2006.01)
(52) U.S. Cl. .......................................... 378/15; 378/91
(58) Field of Classification Search .................... 378/15, 378/91
See application file for complete search history.

(56) References Cited

U.S. PATENT DOCUMENTS

| 3,457,510 A | 7/1969 | Lender |
| 5,010,333 A | 4/1991 | Gardner et al. |
| 5,018,174 A * | 5/1991 | Collins ............................ 378/4 |
| 5,140,696 A * | 8/1992 | Fox .............................. 455/41.1 |
| 5,157,393 A * | 10/1992 | Fox et al. .................... 340/870.3 |
| 5,208,581 A | 5/1993 | Collins |
| 5,530,425 A * | 6/1996 | Harrison ...................... 340/500 |
| 5,577,026 A * | 11/1996 | Gordon et al. ............... 370/278 |
| 5,646,962 A * | 7/1997 | Harrison ...................... 375/308 |
| 5,737,356 A * | 4/1998 | Harrison et al. ............. 375/130 |
| 6,181,766 B1 | 1/2001 | Pearson et al. |
| 6,292,919 B1 * | 9/2001 | Fries et al. .................... 714/758 |
| 6,301,324 B1 * | 10/2001 | Pearson et al. ................. 378/15 |
| 6,362,757 B1 | 3/2002 | Lee et al. |
| 6,433,631 B2 | 8/2002 | Pearson, Jr. et al. |
| 6,956,450 B1 | 10/2005 | Lohr |
| 7,050,616 B2 * | 5/2006 | Hsieh et al. .................. 382/131 |

(Continued)

FOREIGN PATENT DOCUMENTS

WO    2006/043268    4/2006

OTHER PUBLICATIONS

International Search Report for PCT Application No. PCT/EP2008/056558.

*Primary Examiner* — Allen C. Ho
(74) *Attorney, Agent, or Firm* — Meyertons, Hood, Kivlin, Kowert & Goetzel, P.C.; Eric B. Meyertons

(57) ABSTRACT

A rotary joint for transmission of data from a data source to a data sink, between a rotating part and a stationary part, includes a transmission line arrangement fed from a transmission means, and also a receiving means which taps signals from the transmission line arrangement with the aid of a receiving coupler arrangement. A control unit controls the data source. For transmission of data having a small bandwidth an encoder is provided which converts the data from the data source to a duobinary code.

27 Claims, 2 Drawing Sheets

U.S. PATENT DOCUMENTS

| | | | |
|---|---|---|---|
| 7,079,619 B2 * | 7/2006 | Katcha et al. | 378/15 |
| 7,248,641 B2 * | 7/2007 | Schilling et al. | 375/295 |
| 7,274,765 B2 * | 9/2007 | Krumme et al. | 378/15 |
| 7,599,445 B2 * | 10/2009 | Schilling et al. | 375/285 |
| 7,792,231 B2 * | 9/2010 | Popescu | 375/354 |
| 7,844,097 B2 * | 11/2010 | Wegener | 382/131 |
| 7,852,977 B2 * | 12/2010 | Wegener et al. | 378/4 |
| 7,916,830 B2 * | 3/2011 | Wegener et al. | 378/19 |
| 8,045,811 B2 * | 10/2011 | Wegener et al. | 382/232 |
| 8,139,671 B2 * | 3/2012 | Granger et al. | 375/285 |
| 2003/0185427 A1 | 10/2003 | Hsieh et al. | |
| 2004/0102162 A1 | 5/2004 | Krumme et al. | |
| 2005/0012646 A1 | 1/2005 | Kang et al. | |
| 2005/0058461 A1 | 3/2005 | Lee et al. | |
| 2005/0231836 A1 | 10/2005 | Schilling et al. | |

* cited by examiner

NON-CONTACTING ROTARY JOINT

PRIORITY CLAIM

This application is a continuation of pending International Application No. PCT/EP2008/056558 filed May 28, 2008, which designates the United States and claims priority from pending German Application 10 2007 029 109.6 filed on Jun. 21, 2007.

BACKGROUND OF THE INVENTION

1. Field of the Invention

The invention relates to a data transmission system for transmitting data between a rotating part and a stationary part, in particular between the rotating part and the stationary part of a computer tomograph, and also to a computer tomograph having a corresponding transmission system.

2. Description of the Relevant Art

With rotatable units such as radar installations or also computer tomographs, and also with linearly movable units such as crane and conveyor systems it is necessary to transmit electrical signals or energy between units that are movable relative to each other. For this, usually a conductor structure is provided in a first unit, and a suitable tap in a second unit. In the following explanations the term conductor structures refers to all conceivable forms of conductor structures which are suitable for conducting electrical signals. This also refers to the known contacting slide tracks or slip rings. Essential to transmission by means of rotary joints or linear "slide lines" which also may be designed to be non-contacting is a small distance of transmission between the units that are movable relative to each other. Thus a signal can be coupled-out optionally by electrical contact or without contact in a near field of the conductor structures.

A device for data transmission in computer tomographs is known from U.S. Pat. No. 6,433,631 B2. A strip line in a rotating part is supplied with a signal to be transmitted. On the stationary part a tap is provided which is guided along at a small distance of an order of magnitude of about 1 mm from the strip line. With computer tomographs the length of the strip line is of an order of magnitude of about 5 meters. Thus, with data transmission rates of a few tens of gigabits per second, signals having a bandwidth of several gigahertz must be passed through a conductor system having a length of about 5 meters. With this, and particularly at higher frequencies, considerable dielectric losses occur. The dielectric losses are determined by the material of the dielectric of the strip line. Materials having few dielectric losses are extremely expensive, and usually also difficult to machine.

A duobinary encoder is disclosed in U.S. Pat. No. 3,457,510. This consists of a digital logic followed by a band-pass filter.

A capacitive rotary joint having a band-pass characteristic is disclosed in EP 1 012 899 A. This is a band-pass filter of high order, having extremely steep filter flanks.

A duobinary pre-coder is disclosed in WO 2006/043268 A1.

SUMMARY OF THE INVENTION

Embodiments herein relate to a computer tomograph having a rotary joint system, and also a rotary joint system, for example for computer tomographs, in which low-cost dielectric materials having higher attenuations at higher frequencies can be used for the television-line structure (strip line).

In one embodiment, a computer tomograph includes a rotating part, a stationary part, and a rotary joint with a transmission line arrangement and a receiving coupler arrangement for transmission of electrical signals between the rotating part and the stationary part; with the computer tomograph further including:
  at least one data source;
  at least one digital encoder for converting signals from the data source to duobinary encoded signals;
  at least one filter for matching the encoded signals to transmission characteristics of the rotary joint, so that a transmission function of the rotary joint together with the at least one filter represents a band-pass filter needed for duobinary encoding;
  at least one driver which matches signals from the filter to electrical characteristics of the transmission line arrangement and feeds these signals into the transmission line arrangement;
  at least one amplifier for amplifying signals from the receiving coupler arrangement; and
  at least one receiver which decodes signals from the amplifier and conditions these signals for relay to a data sink.

In one embodiment, a computer tomograph includes a rotating part, a stationary part, and a rotary joint with a transmission line arrangement and a receiving coupler arrangement for transmission of electrical signals between the rotating part and the stationary part; with the computer tomograph further including:
  at least one data source;
  at least one encoder for converting signals from the data source to mb810 encoded signals;
  at least one filter for matching the encoded signals to transmission characteristics of the rotary joint;
  at least one driver which matches signals from the filter to electrical characteristics of the transmission line arrangement, and feeds these signals into the transmission line arrangement;
  at least one amplifier for amplifying signals from the receiving coupler arrangement; and
  at least one receiver which decodes signals from the amplifier and conditions these signals for relay to a data sink.

In one embodiment, a rotary joint for transmitting electrical signals between a rotating part and a stationary part, includes a transmission line arrangement and a receiving coupler arrangement; with the rotary joint further including:
  at least one digital encoder for converting signals from a data source to duobinary encoded signals;
  at least one filter for matching the encoded signals to transmission characteristics of the rotary joint, so that a transmission function of the rotary joint together with the at least one filter represents a band-pass filter needed for duobinary encoding;
  at least one driver which matches signals from the filter to electrical characteristics of the transmission line arrangement and feeds these signals into the transmission line arrangement;
  at least one amplifier for amplifying signals from the receiving coupler arrangement; and
  at least one receiver which decodes signals from the amplifier and conditions these signals for relay to a data sink.

Furthermore, in another embodiment, a rotary joint for transmitting electrical signals between a rotating part and a stationary part, includes a transmission line arrangement and a receiving coupler arrangement; with the rotary joint further including:

at least one encoder for converting signals from a data source to mb810 encoded signals, or run length limited (RLL) encoded signals such as 8b13bRLL(2,15);

at least one filter for matching the encoded signals to transmission characteristics of the rotary joint;

at least one driver which matches signals from the filter to electrical characteristics of the transmission line arrangement and feeds these signals into the transmission line arrangement;

at least one amplifier for amplifying signals from the receiving coupler arrangement;

at least one receiver which decodes signals from the amplifier and conditions these signals for relay to a data sink.

BRIEF DESCRIPTION OF THE DRAWINGS

In the following the invention is described by way of example, without limitation of the general inventive concept, on examples of embodiment and with reference to the drawings.

Figure 1:
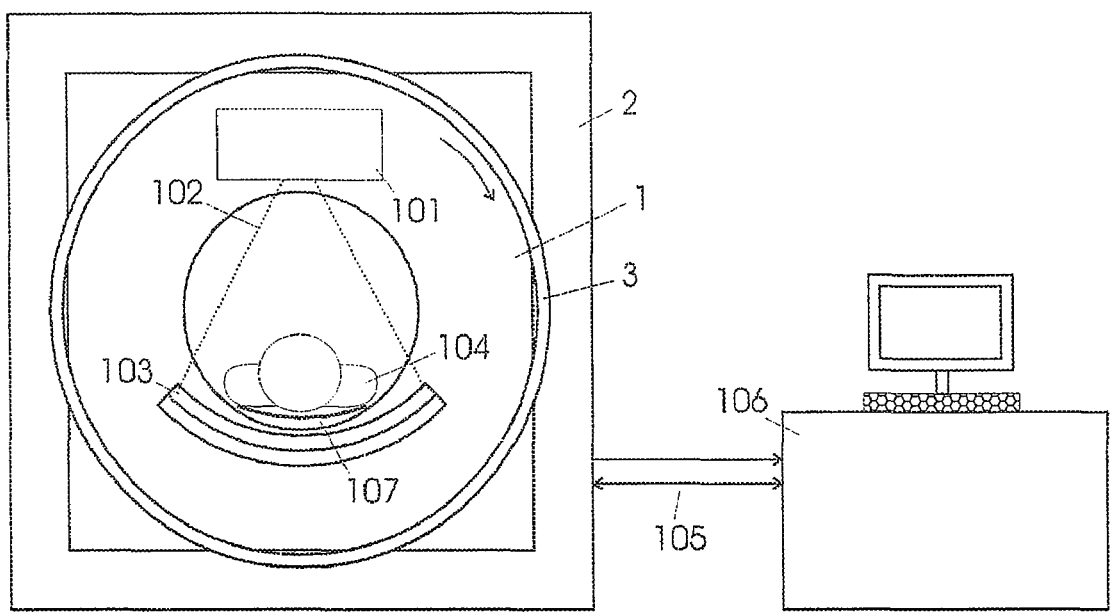
FIG. 1 schematically shows in a general form a computer tomograph.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE DRAWINGS

FIG. 1 shows an example of a computer tomograph. The computer tomograph (CT scanner) consists of two main mechanical components. A stationary part 2 serves as a base and support of the entire instrument in which the rotating part revolves. A patient 104 is positioned on a berth 107 inside an opening on the rotating part. An X-ray tube 101 and also a detector 103 disposed opposite thereto are provided for scanning the patient by means of X-rays 102. X-ray tube 101 and detector 103 are disposed on the rotating part 1 to be rotatable. A rotary joint 3 serves for electrical connection between the rotating part 1 and the stationary part 2. With this, on the one hand, high electrical power for feeding the X-ray tube 101 is transmitted in a direction towards the rotating part 1, and simultaneously raw data of an image are transmitted in an opposite direction. Communication of control information in both directions is provided parallel thereto. An evaluation and control unit 106 serves for operating the computer tomograph and also for displaying generated images. Communication with the computer tomograph is effected via a bidirectional link 105.

Figure 2:
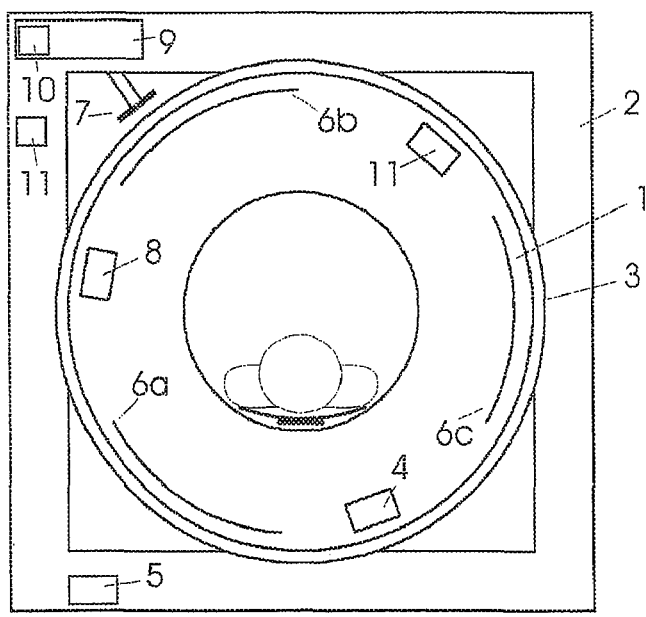
FIG. 2 schematically shows the arrangement of transmitting/receiving means.

FIG. 2 shows in a simplified form an example of an arrangement of a computer tomograph together with components needed for transmission. The data from a data source 4 (detector 103 with subsequent signal processing or DAS) on the rotating part 1 are conditioned by means of a first transmitting means 8 and relayed to the transmission line arrangement which is here illustrated by way of example as consisting of three parts 6a, 6b, 6c. This transmission line arrangement now carries the high-frequency signals. These are tapped-off by the receiving coupler arrangement 7. Illustrated by way of example is a receiving coupler arrangement which is firmly connected to the stationary frame. The signals picked-up from this receiving coupler arrangement 7 are relayed to a first receiving means 9 for conditioning. The output signals from the latter are then conducted to a data sink 5.

This Figure illustrates by way of example the PLL 10 in the receiving means 9. Similarly, and alternatively or additionally, a PLL could be present in the data sink 5.

Figure 3:
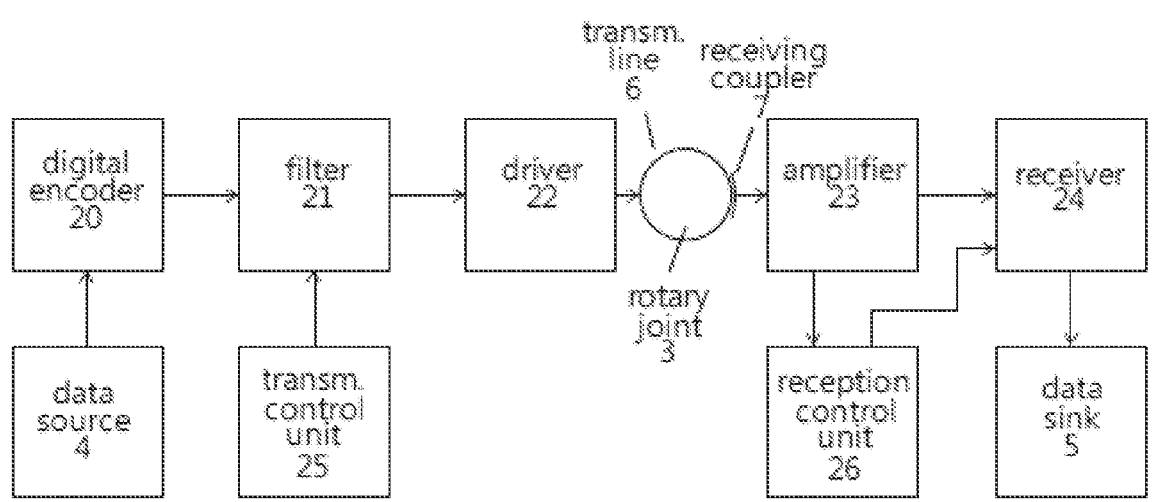
FIG. 3 shows the block circuit diagram of an arrangement.

FIG. 3 shows the block circuit diagram. Signals from the data source 4 are converted by means of an encoder 20 to duobinary signals. A matching to the transmission characteristics of the data path is effected by means of the filter 21. The levels of the signals from the filter 21 are then matched to the impedance and electrical characteristics of the transmission line arrangement 6 of the rotary joint 3 by means of a driver 22, and the signals are coupled into this transmission line arrangement 6. The receiving coupler arrangement 7 is disposed to be rotatable relative to the transmission line arrangement 6, and serves for tapping-off the electrical signals which are conducted along the transmission line arrangement. The electrical signals tapped-off by the receiving coupler arrangement 7 are now pre-amplified via an amplifier 23 and supplied to a receiver 24, and also optionally to a control unit 26. The receiver 24 decodes the duobinary encoded signals. For this, it can with advantage include an adjustable amplification, an adjustable filter particularly an adaptive filter, and also adjustable threshold values. A control of these values or filters can be effected by means of the control unit 26 in dependence upon various measurement parameters. Measurement parameters of this kind can be, for example, the signal amplitude of the input signal from the amplifier 23, the eye pattern, or also the position of the receiving coupler arrangement 7 relative to the feeding-in point of the driver 22 into the transmission line arrangement 6. The evaluated signal from the receiver 24 is then supplied to the data sink 5 for further processing. In order to improve the transmission characteristics of the entire arrangement, a transmission control unit 25 is also provided optionally on the side of the rotating part 1. This control unit controls preferably the filter 21, but optionally also other components on the rotating part. It is of special advantage for control of the filter 21 to be effected for pre-emphasizing high-frequency signal components in dependence upon the attenuation of the transmission line arrangement, or in dependence upon the position of the receiving coupler arrangement relative to the feeding-in point of the driver 22 into the transmission line arrangement 6.

DETAILED DESCRIPTION OF THE PREFERRED EMBODIMENTS

A computer tomograph is illustrated here by way of example. Data are transmitted between a rotating part 1 and a stationary part 2 of a computer tomograph. At least one data source 4 is provided on the rotating part, and at least one data sink 5 on the stationary part. A data source can be, for example, an X-ray detector 103 or its DAS (Data Acquisition System), or also any desired other control means, or a computer. Data from a plurality of data sources also can be combined with each other for transmission. A data sink can be a computer 106 for evaluating and conditioning the data, but also another control unit.

The rotary joint includes in the rotating part at least one first transmitting means 8, and also one transmission line arrangement 6 fed thereby. A first transmitting means of this kind receives data from the data source and converts these for transmission by the transmission line arrangement. The transmission line arrangement includes at least one conductor for conducting electro-magnetic waves, which conductor is preferably mounted along at least one circular segment or a circular track on the rotating part. The transmission line arrangement can include, for example, mechanical slip-rings, non-conducting electrical coupling elements such as inductive or capacitive coupling elements, or also light-waveguides. Similarly, the transmission line arrangement can include a combination of a plurality of different coupling elements.

Furthermore, in the stationary part the rotary joint includes at least one first receiving means 9 and, for feeding this, also one receiving coupler arrangement 7.

The couplers are designed to match the transmission line arrangement. Thus, for example, capacitive coupling faces together with a strip line structure can be used as a transmission line arrangement. Similarly, also optical prism couplers together with a light-waveguide, for example such as a mirror trench, can be combined to form a transmission line arrangement.

The receiving means 9 converts the signals received by the receiving coupler arrangement 7 from the transmission line arrangement 6 for relay to the data sink.

The receiving means 9 and/or the data sink 5 include a PLL 10 for synchronizing the internal received clock with a received data stream. Furthermore, a control unit 11 is provided for controlling the at least one data source 4 and/or the at least one transmitting means 8. The control unit can be disposed on any one of the parts that are rotatable relative to each other, or also divided onto both parts. The control unit signals a fault in reception by the receiving means, and/or an unlocking of the PLL, and causes an emission of a specific resynchronization signal. Here the resynchronization signal can be generated optionally by the data source which emits the data particularly suited for resynchronization. Similarly, however, also the transmitting means can generate the resynchronization signal independently from the data supplied by the data source. Even when a synchronization signal is generated instead of the payload data supplied from the data source, this leads to no additional loss of data, because in no case can data be transmitted with an unsynchronized PLL.

The here described, particularly favorable embodiment of a computer tomograph can be used appropriately also for other applications for transmitting signals from a data source to a data sink that is rotatable or linearly movable relative thereto. Examples of application are general rotary joints as used in radar installations, rotary transfer installations, or cranes. Also data concerning slip-rings or slide lines can be transmitted.

Transmitting means 8 includes an encoder 20, a filter 21, and also a driver 22. The signals from the data source 4 are converted to duobinary encoded signals for transmission via the rotary joint. A suitable duobinary encoder is disclosed for example in U.S. Pat. No. 3,457,510. With this duobinary encoding, signals having a lower bandwidth than those with an NRZ encoding can be transmitted. A duobinary code is a code of the Class of Correlated Codes. The duobinary encoding is effected in a first step by a digital encoding stage, and in a second step by band-pass filtering of the encoded digital signals. An encoding stage of this kind can be also a pre-coder. The first step is implemented with the digital encoder 20. Furthermore, the necessary filtering of the signals is effected by means of the filter 21 together with the transmission line arrangement 6. Known transmission line arrangements typically have a band-pass characteristic. An example is disclosed in EP 1 012 899 A. The band-pass filter necessary for the duobinary encoding is now formed by the filter 21 and the transmission line arrangement 6. Preferably this band-pass filter causes a minimal transmission loss at one-quarter of the bit rate of the digital data. A high transmission loss should be provided at zero frequency, and at a frequency corresponding to the half-bit rate of the digital data. The output signal of the filter 21 is transmitted via the driver 22 to the transmission line arrangement 6. It is the purpose of the driver 22 to make available a signal of sufficiently large amplitude for a load corresponding to the transmission line arrangement 6. Here the driver is preferably a linear amplifier. An arrangement having a digital driver following the encoding stage, and also a filter connected to follow the driver, can be implemented. Usually the transmission line arrangements have relatively low impedances in a range of a few ohms, and typically in a range of 10 to 100 ohms. Here a suitable matching is effected by the driver 22. Furthermore, in a preferred manner it is a purpose of the driver 22 to make available balanced signals for feeding a differential transmission line arrangement. When a differential transmission line arrangement is used, a relatively low emission of high-frequency signals into free space can be achieved. With this, favorable EMC properties can be attained. However, a prerequisite for this is a highly balanced differential signal. In order to generate this, the driver preferably also has means for balancing the signal, such as for example balancing transformers or baluns. Similarly, a pre-coder as disclosed in WO 2006/043268 can be also used.

A receiving means 9 includes at least one amplifier 23 and a receiver 24. The amplifier 23 amplifies the signals from the receiving coupler arrangement 7. As the receiving coupler arrangement 7 typically has very small coupling faces, the coupling capacity to the transmission line arrangement 6 is relatively small. Accordingly, the transmitted power is low. This must now be amplified by a suitable preliminary amplifier. Furthermore, the amplifier 23 is advantageously provided with a device for increasing the common mode rejection. This can be, for example, a balancing transformer or a balun. Thus, only push-pull signals corresponding to the specific data to be transmitted by the transmission line arrangement 6 are further processed. Interference which is coupled into the arrangement from the outside consists preferably of common mode signals which are then filtered-off. The receiver 24 evaluates the signals from the amplifier 23 and generates a data stream which can be processed further by the data sink 5. For this, the receiver 24 includes a duobinary converter for decoding the duobinary signals. Preferably the receiver contains a value-forming element for forming optionally the value of the signal voltage or the signal power. Furthermore, the receiver 24 can include a filter arrangement for compensating the frequency response of the entire arrangement, in particular that of the transmission line arrangement 6. Here preferably also higher frequency components which are strongly attenuated in the transmission line arrangement 6 are pre-emphasized. This is expedient in particular when the second step of the duobinary encoding, i.e. the filtering by the filter 21, is effected solely by the filter 21. This can be the case, for example, when the transmission characteristics of the transmission line arrangement 6 are not known, or fluctuate strongly. Similarly, further filtering measures for suppressing interference can be provided.

In an embodiment, the transmitting means 8 also includes an additional transmission control unit 25. With this, preferably the filter 21 can be controlled. With an arrangement in accordance with embodiments described herein an especially large problem is the strong fluctuation of the transmission function of the transmission line arrangement 6. In the following this is described on two extreme states. In the first case the receiving coupler arrangement 7 is located at the feeding-in point of the driver 22 into the transmission line arrangement 6. At this location the fed-in signal travels no, or only a negligibly small, distance in the transmission line arrangement 6. Accordingly, also the frequency-dependent attenuation by the transmission line arrangement is negligible. Here practically no frequency response correction is necessary for achieving an optimal signal transmission. The other extreme position is at the point at which the receiving coupler arrangement has the greatest distance from the coupling-in location of the driver into the transmission line arrangement 6. This is often that point on the rotary joint which is exactly opposite to the coupling-in position. At this location the electric signal passes along one-half of the periphery of a rotary joint 3 and thus along one-half of the line length of the transmission line arrangement 6. Here a very strongly frequency-dependent attenuation of the signal by the transmission line arrangement 6 results. Particularly in the case of the transmission line arrangement disclosed in EP 1 012 899 A, an only very small band-pass effect results when a signal is coupled-out at the location of feeding-in, because the signal has not yet passed through any one of the filter elements of meandering configuration. When the signal is coupled-out opposite to the location of feeding-in, it has already passed through a large number of filter elements. Accordingly, a band-pass filtering of higher order results at the location of coupling-out of the signal. The filter 21 is now controlled by the transmission control unit 25 according to the filter action, or the position of the location of coupling-out, so that it at least substantially compensates the filter action of the transmission line arrangement 6, and a preferably constant transmission function results. Alternatively, or in addition to this, a control of the driver 22 also could be effected instead of the control of a filter. The control by the transmission control unit 25 is effected in dependence on position, for example. Thus the attenuation characteristic of the transmission line arrangement is known and can be measured, for example when the entire arrangement is taken into operation. Thus, a position-dependent correction value that is generated either from a measured value memory, or also by calculation, can be pre-set for the filter 21. The determination of the position, i.e. the path length between the receiving coupler arrangement 7 and the point of feeding-in of the signals from the driver 22 into the transmission line arrangement 6 can be effected with a position encoder, or also by a time measurement at constant or known rotation speed. Another embodiment includes a receiver which has a reception control unit 26. This control unit optimizes the threshold-value setting of the detector in the receiver, and can control this detector additionally to make a frequency-dependent correction. For this, the control unit 26 receives signals from the amplifier 23. In a simple case the control unit 26 could, for example, have a device for determining the signal amplitude of the signal from the amplifier 23, or perform an evaluation of the eye pattern. The switching thresholds of the decoder for decoding the duobinary signals then could be matched accordingly in the receiver 24. As an alternative to this, also an amplification factor could be set accordingly in the receiver 24, so that the receiver can decode the signals with errors that are as small as possible using fixed given switching thresholds. Furthermore, with the control unit 26 also an additional frequency response compensation could be performed in the receiver. Thus, the control unit can advantageously determine the spectral composition of the signal, and from this can signal to the receiver 24 a compensation value, in particular for pre-emphasizing high-frequency signal components. In addition or as an alternative to a spectral evaluation, also an evaluation of the position of the feeding-in point of the driver 22 into the transmission line arrangement 6 relative to the receiving coupler arrangement 7 can be made use of. This can be effected in a way similar to that previously described in connection with the transmission control unit 25.

In the descriptions concerning the transmission function or the attenuation, reference was made for reasons of clarity to the transmission function of the transmission line arrangement 6, because this, as disclosed for example in EP 1 012 899 A, has the largest effect on the entire transmission function of the rotary joint 3. Of course, the transmission function of the rotary joint 3 is determined by all of its components, in particular the transmission line arrangement 6 and the receiving coupler arrangement 7.

In another embodiment, an mb810 encoding or a different line code is used, for example 8b13bRLL(3,15). The mb810 encoding offers an output signal with a frequency spectrum that is favorable under EMC aspects. Accordingly, then an appropriate linking with the pseudo random signal should be provided following the encoding, in order to reconstruct the original signal. As an alternative to the RLL codes, 8b12b, 8b13b, or 8b16 encodings can be used. It is of special advantage to perform first an mb810 encoding of the data, and then to perform a duobinary encoding with the thus encoded data.

In another embodiment, additionally at least one multiplexer is provided for combining at least two signals to a common duobinary encoded signal. Advantageously, this multiplexer has also a FIFO or a digital buffer memory for reducing the entire jitter. The data stored in this are then transmitted via the rotary joint in a duobinary encoded state.

In addition to a duobinary encoding, a digital encoding, for example in an 8b10b or an 64b66b code, can be performed first.

In order to simplify the presentation, in the present document reference is made to a transmission from a rotary part to a stationary part of a computer tomograph. Of course, a device as described herein can be used also in an opposite direction of transmission. Similarly, a device as described herein can be used also in other applications for rotary transmission, and also for linear transmission between two units that are movable relative to each other.

A method for transmitting data between the rotating part 1 and the stationary part 2 of a computer tomograph having a rotary joint 3 for transmission of electrical signals with a transmission line arrangement 6 and a receiving coupler arrangement 7 includes the following steps:

(a) Converting signals from a data source 4 with at least one encoder 20 to duobinary and/or mb810 encoded signals;

(b) filtering the encoded signals with at least one filter 21 for matching to the transmission characteristics of the rotary joint 3;

(c) conforming the signals from the filter 21 to the electrical properties of the transmission line arrangement 6 and feeding these signals into the transmission line arrangement 6 by means of at least one driver 22;

(d) amplifying the signals from the receiving coupler arrangement 7 by means of at least one amplifier 23;

(e) decoding and conditioning the signals from the amplifier 23 for relay to a data sink 5 by means of at least one receiver 24.

Preferably the filtering of the signal by means of the filter 21 is here effected so that the transmission function of the filter 21 together with the transmission function of the transmission line arrangement 6 corresponds to the filter characteristic as needed for the duobinary encoding.

The direction of transmission as set out here was chosen to be that from the rotor to the stator, because this corresponds to the most frequent case of application. However, transmission in the opposite direction, or bidirectional transmission, is similarly possible. For the sake of clarity, no distinction is made in the present document between a transmission between units that are movable relative to each other, and a transmission between a stationary unit and units movable relative thereto, because this is only a question of reference to locality and has no effect upon the manner of functioning.

A compilation of principles of encoding with optical transmission paths can be found in Michel et al., "Ein 16 Gbit/s Duobinary Precoder Chip in SiGe-Technologie sowie Möglichkeiten innovativer Aufbau- und Montagetechniken" ("A 16 Gbit/s Duobinary Precoder Chip in SiGe Technology and also Possibilities of Innovative Construction and Assembly Techniques"), lecture given on Jun. 21, 2007 at EEEfCOM 2007 in Ulm. This is incorporated herein by reference.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. Computer tomograph, comprising a rotating part, a stationary part, and a rotary joint with a transmission line arrangement and a receiving coupler arrangement for transmission of electrical signals between the rotating part and the stationary part; with the computer tomograph further comprising:
   at least one data source;
   at least one digital encoder for converting signals from the data source to duobinary encoded signals;
   at least one filter for matching the encoded signals to transmission characteristics of the rotary joint, so that a transmission function of the rotary joint together with the at least one filter represents a band-pass filter needed for duobinary encoding;
   at least one driver which matches signals from the at least one filter to electrical characteristics of the transmission line arrangement and feeds these signals into the transmission line arrangement;
   at least one amplifier for amplifying signals from the receiving coupler arrangement;
   at least one data sink; and
   at least one receiver which decodes signals from the at least one amplifier and conditions these signals for relay to the at least one data sink.

2. Computer tomograph comprising a rotating part, a stationary part, and a rotary joint with a transmission line arrangement and a receiving coupler arrangement for transmission of electrical signals between the rotating part and the stationary part; with the computer tomograph further comprising:
   at least one data source;
   at least one encoder for converting signals from the data source to mb810 encoded signals;
   at least one filter for matching the encoded signals to transmission characteristics of the rotary joint;
   at least one driver which matches signals from the at least one filter to electrical characteristics of the transmission line arrangement, and feeds these signals into the transmission line arrangement;
   at least one amplifier for amplifying signals from the receiving coupler arrangement;
   at least one data sink; and
   at least one receiver which decodes signals from the at least one amplifier and conditions these signals for relay to the at least one data sink.

3. Rotary joint for transmitting electrical signals between a rotating part and a stationary part, comprising a transmission line arrangement and a receiving coupler arrangement; with the rotary joint further comprising:
   at least one digital encoder for converting signals from a data source to duobinary encoded signals;
   at least one filter for matching the encoded signals to transmission characteristics of the rotary joint, so that a transmission function of the rotary joint together with the at least one filter represents a band-pass filter needed for duobinary encoding;
   at least one driver which matches signals from the at least one filter to electrical characteristics of the transmission line arrangement and feeds these signals into the transmission line arrangement;
   at least one amplifier for amplifying signals from the receiving coupler arrangement;
   at least one data sink; and
   at least one receiver which decodes signals from the at least one amplifier and conditions these signals for relay to the at least one data sink.

4. Rotary joint according to claim 3, wherein the at least one encoder first converts the signals from the data source to mb810 or run length limited (RLL) encoded signals, and subsequently converts them to duobinary encoded signals.

5. Rotary joint according to claim 3, wherein a transmission control unit is provided for at least controlling the at least one filter so that matching to the transmission characteristics of the rotary joint is effected.

6. Rotary joint according to claim 5, wherein the transmission control unit at least controls the at least one filter in dependence upon a position of the receiving coupler arrangement with respect to a feeding-in point of the at least one driver into the transmission line arrangement.

7. Rotary joint according to claim 5, wherein the transmission control unit at least controls the at least one filter in dependence upon signal attenuation in a transmission path of the rotary joint.

8. Rotary joint according to claim 3, wherein a transmission control unit is provided for at least controlling the at least one filter so that a pre-emphasis of higher frequencies is effected.

9. Rotary joint according to claim 8, wherein the transmission control unit at least controls the at least one filter in dependence upon a position of the receiving coupler arrangement with respect to a feeding-in point of the at least one driver into the transmission line arrangement.

10. Rotary joint according to claim 8, wherein the transmission control unit at least controls the at least one filter in dependence upon signal attenuation in a transmission path of the rotary joint.

11. Rotary joint according to claim 3, wherein a reception control unit is provided for at least controlling the at least one receiver so that matching to the transmission characteristics of the rotary joint is effected.

12. Rotary joint according to claim 11, wherein the reception control unit sets at least one of a switching threshold and an amplification value for the at least one receiver.

13. Rotary joint according to claim 12, wherein the reception control unit sets at least one of a switching threshold and an amplification value in dependence upon a position of the receiving coupler arrangement with respect to a feeding-in point of the at least one driver into the transmission line arrangement.

14. Rotary joint according to claim 12, wherein the reception control unit sets at least one of a switching threshold and an amplification value in dependence upon an attenuation of the rotary joint or an amplitude of an input signal from the receiving coupler arrangement.

15. Rotary joint for transmitting electrical signals between a rotating part and a stationary part, comprising a transmission line arrangement and a receiving coupler arrangement; with the rotary joint further comprising:
- at least one encoder for converting signals from a data source to mb810 encoded signals, or run length limited (RLL) encoded signals;
- at least one filter for matching the encoded signals to transmission characteristics of the rotary joint;
- at least one driver which matches signals from the at least one filter to electrical characteristics of the transmission line arrangement and feeds these signals into the transmission line arrangement;
- at least one amplifier for amplifying signals from the receiving coupler arrangement;
- at least one data sink; and
- at least one receiver which decodes signals from the at least one amplifier and conditions these signals for relay to the at least one data sink.

16. Rotary joint according to claim 15, wherein the at least one encoder first converts the signals from the data source to mb810 or run length limited (RLL) encoded signals, and subsequently converts them to duobinary encoded signals.

17. Rotary joint according to claim 15, wherein a transmission control unit is provided for at least controlling the at least one filter so that matching to the transmission characteristics of the rotary joint is effected.

18. Rotary joint according to claim 17, wherein the transmission control unit at least controls the at least one filter in dependence upon a position of the receiving coupler arrangement with respect to a feeding-in point of the at least one driver into the transmission line arrangement.

19. Rotary joint according to claim 17, wherein the transmission control unit at least controls the at least one filter in dependence upon signal attenuation in a transmission path of the rotary joint.

20. Rotary joint according to claim 15, wherein a transmission control unit is provided for at least controlling the at least one filter so that a pre-emphasis of higher frequencies is effected.

21. Rotary joint according to claim 20, wherein the transmission control unit at least controls the at least one filter in dependence upon a position of the receiving coupler arrangement with respect to a feeding-in point of the at least one driver into the transmission line arrangement.

22. Rotary joint according to claim 20, wherein the transmission control unit at least controls the at least one filter in dependence upon signal attenuation in a transmission path to the rotary joint.

23. Rotary joint according to claim 15, wherein a reception control unit is provided for at least controlling the at least one receiver so that matching to the transmission characteristics of the rotary joint is effected.

24. Rotary joint according to claim 23, wherein the reception control unit sets at least one of a switching threshold and an amplification value for the at least one receiver.

25. Rotary joint according to claim 24, wherein the reception control unit sets at least one of a switching threshold and an amplification value in dependence upon a position of the receiving coupler arrangement with respect to a feeding-in point of the at least one driver into the transmission line arrangement.

26. Rotary joint according to claim 24, wherein the reception control unit sets at least one of a switching threshold and an amplification value in dependence upon an attenuation of the rotary joint or an amplitude of an input signal from the receiving coupler arrangement.

27. Method for transmitting data between a rotating part and a stationary part of a computer tomograph having a rotary joint for transmitting electrical signals with a transmission line arrangement and a receiving coupler arrangement, comprising the following steps:
- converting signals from a data source with at least one encoder to at least one of duobinary encoded signals, mb810 encoded signals, and run length limited (RLL) encoded signals;
- filtering the encoded signals with at least one filter for matching to transmission characteristics of the rotary joint;
- matching signals from the at least one filter to electrical characteristics of the transmission line arrangement, and feeding these signals into the transmission line arrangement with at least one driver;
- amplifying signals from the receiving coupler arrangement with at least one amplifier; and
- decoding and conditioning signals from the at least one amplifier with at least one receiver, for relay to a data sink.

* * * * *